United States Patent
Osornio Lopez et al.

(10) Patent No.: US 9,096,129 B2
(45) Date of Patent: Aug. 4, 2015

(54) METHOD AND SYSTEM FOR FACILITATING VIEWING OF INFORMATION IN A MACHINE

(71) Applicant: Freescale Semiconductor, Inc., Austin, TX (US)

(72) Inventors: Victor Hugo H. Osornio Lopez, Guadalajara (MX); Francisco C. Sandoval Zazueta, Northville, MI (US); Michael A. Staudenmaier, Munich (DE)

(73) Assignee: FREESCALE SEMICONDUCTOR, INC., Austin, TX (US)

(*) Notice: Subject to any disclaimer, the term of this patent is extended or adjusted under 35 U.S.C. 154(b) by 36 days.

(21) Appl. No.: 13/953,478

(22) Filed: Jul. 29, 2013

(65) Prior Publication Data
US 2015/0029013 A1    Jan. 29, 2015

(51) Int. Cl.
| | | |
|---|---|---|
| B60Q 1/00 | (2006.01) | |
| B60K 35/00 | (2006.01) | |
| G06K 9/00 | (2006.01) | |
| A61B 5/18 | (2006.01) | |
| B60K 28/06 | (2006.01) | |

(52) U.S. Cl.
CPC . *B60K 35/00* (2013.01); *A61B 5/18* (2013.01); *B60K 28/066* (2013.01); *G06K 9/00845* (2013.01)

(58) Field of Classification Search
CPC .......... G08B 21/06; A61B 5/18; B60K 28/06; B60K 28/066
USPC .................. 340/438, 439, 575, 576; 180/272
See application file for complete search history.

(56) References Cited

U.S. PATENT DOCUMENTS

| | | | |
|---|---|---|---|
| 5,583,795 A * | 12/1996 | Smyth ........................ | 702/150 |
| 7,591,558 B2 | 9/2009 | Wezowski et al. | |
| 7,800,625 B2 | 9/2010 | Liu et al. | |
| 8,209,635 B2 | 6/2012 | ThöM | |

(Continued)

FOREIGN PATENT DOCUMENTS

EP         2021899 A1    2/2009

OTHER PUBLICATIONS

Android Eye Detection and Tracking with OpenCV; http://romanhosek.cz/android-eye-detection-and-tracking-with-opencv/; posted Jan. 28, 2013; 14 pages.

(Continued)

*Primary Examiner* — John A Tweel, Jr.

(57) ABSTRACT

Methods and systems for facilitating viewing of information by machine users associated with machines, such as vehicle users in vehicles, are disclosed. In one example embodiment, a method for facilitating viewing of first information comprises (a) determining second information concerning a viewing direction of the machine user, and (b) adapting at least one operation of at least one display device so as to display the first information. Also, in an additional example embodiment, the method further comprises (c) additionally determining whether a first condition has been met, where the first condition is indicative of whether the machine user has failed to view in a sufficient manner the first information for or during a first predetermined amount of time. Additionally, the method comprises (d), upon the first condition being additionally determined to have been met, one or both of (i) repeating (a), (b), and (c), and (ii) outputting a signal configured to be sensed by the machine user.

20 Claims, 4 Drawing Sheets

(56) References Cited

U.S. PATENT DOCUMENTS

| | | | |
|---|---|---|---|
| 8,564,533 B2* | 10/2013 | Yuan | 345/156 |
| 2005/0229200 A1 | 10/2005 | Kirkland et al. | |
| 2008/0161997 A1* | 7/2008 | Wengelnik et al. | 701/36 |
| 2011/0285982 A1* | 11/2011 | Breed | 356/4.01 |
| 2012/0154441 A1* | 6/2012 | Kim | 345/633 |
| 2012/0271484 A1* | 10/2012 | Feit et al. | 701/1 |
| 2014/0129987 A1* | 5/2014 | Feit et al. | 715/835 |

OTHER PUBLICATIONS

Read My Eyes, a Presentation of the ITU Gaze Tracker; Gaze Tracker Development; http://www.gazegroup.org/develop/; May 9, 2011; 6 pages.

Zhang, W. et al.; A Method of Gaze Direction Estimation Considering Head Posture; Int'l Journal of Signal Processing, Image Processing and Pattern Recognition; vol. 6. No. 2, Apr. 2013; pp. 103-112.

Wild, D.; Gaze Tracking Using a Regular Web Camera; Rhodes University; Nov. 2012; 64 pages.

* cited by examiner

METHOD AND SYSTEM FOR FACILITATING VIEWING OF INFORMATION IN A MACHINE

CROSS-REFERENCE TO RELATED APPLICATIONS

N/A

STATEMENT REGARDING FEDERALLY SPONSORED RESEARCH OR DEVELOPMENT

N/A

FIELD OF THE DISCLOSURE

The present disclosure relates to methods and systems for displaying information and, more particularly, relates to methods and systems for displaying information for viewing in a machine by machine operators (or other persons in or associated with the machine) in a manner that facilitates view of the information.

BACKGROUND OF THE DISCLOSURE

Vehicles such as automobiles are increasingly capable of sensing, monitoring, calculating, and/or otherwise obtaining a variety of types of information about a variety of issues including, for example, issues related to vehicle status and vehicle performance. Much if not all of this information can be of interest to vehicle operators (e.g., the driver of a vehicle), and many vehicles are now equipped with numerous display devices that are configured to display such information for viewing by vehicle operators. Such vehicles can include, for example, one or more display devices integrated into the dashboard, steering wheel, or console of a vehicle, as well as display devices that project or otherwise generate images for viewing on the windshield of a vehicle. At least some vehicles include "high end automotive cluster devices" that include multiple display devices and that are configured to convey information to vehicle operators.

Notwithstanding the presence of such display devices in vehicles, and notwithstanding the capability of such display devices to display information that is of interest or use to vehicle operators, conventional implementations of such display devices are still inadequate in certain respects. More particularly, even though information may be displayed for viewing by vehicle operators, it is often (if not usually) the case that vehicle operators will miss or fail to appreciate the significance of certain important portions of information. Indeed, vehicle operators can be distracted, can become oblivious to information being displayed, or even can be overwhelmed by the amount of information that is displayed, such that the vehicle operators fail to be attentive to those portions of information that are of particular importance. Although some conventional vehicles include an additional feature according to which, if information deemed to be important is being displayed, a sound is output that is intended to attract a vehicle operator's attention, such operation still may be insufficiently reliable as a basis for presuming that the vehicle operator has viewed the important information.

DETAILED DESCRIPTION

The present disclosure relates to methods and systems for displaying information in vehicles and, more particularly, for facilitating the viewing of such displayed information by vehicle operators (e.g., drivers) or other persons or users within or associated with the vehicle. In at least some embodiments, the present disclosure is intended to facilitate viewing of displayed information in a manner that ensures or enhances the likelihood that important (or even critical) messages or other important portions of the displayed information are viewed by or conveyed/delivered to the vehicle operator (and/or to other persons or users within or associated with the vehicle), in a manner that avoids adding significant distractions. Further, in at least some embodiments, the present disclosure relates to a method and system (or apparatus) for detecting if the vehicle operator (or other person or user) has a clear view of the information that is being displayed in a cluster of display devices, and displaying the information at a convenient point. If a line of sight of the vehicle operator (or other person or user) is such that the vehicle operator will not be able to see all content on the cluster, then the method and system operates to dynamically rearrange the position(s) at which the information is displayed, to ensure or increase the likelihood that the information is displayed in a visible zone.

Additionally, in at least some embodiments, the method and system operates to detect that a message or other information has been observed, or to make a determination that the message or other information probably or likely has been observed based upon some other criterion, such as whether the vehicle operator (or other person or user) is positioned in a manner that suggests that the message or other information probably or likely has been observed. If the method and system does not detect that observation has occurred, or make a determination that observation probably or likely has been observed, then the method and system further operates to trigger other signals, for example, audio signals or tactile feedback (e.g., via light steering wheel vibrations) that are intended to cause the vehicle operator to take note that there is information that should be viewed and ultimately to cause the vehicle operator to observe that information. Also, in some embodiments, the method and system can operate to ensure that information has been observed or received by the vehicle operator (or other person or user) by operating to require that an express acknowledgement signal be provided by the vehicle operator (or other person or user), for example, by way of the operator's pressing of a button or verbally acknowledging receipt of the information.

As will be apparent from the further discussion provided below, at least some embodiments encompassed herein envision a system that includes a camera, one or more speakers and/or a steering wheel rumbling motor (or other steering wheel vibration device), one or more display devices that are capable of directly or indirectly (e.g., by way of projection)

causing the display of content or information at one or more display regions, and one or more computing, control, or processing devices or units that are configured to perform, among other things, line of sight detection and control over the display of content/information.

In at least some embodiments, the camera will monitor where a vehicle operator or driver (or other person or user with or associated with a vehicle) is looking at. When an important message or other content or information of interest such as a low fuel alert needs to be conveyed to the vehicle operator (or other person or user), the line of sight information is used to determine which display region or display regions is or are the most likely to be seen. Correspondingly, a display device or display devices governing the display of information at that display region or regions will also be identified or selected. Once the display region(s) and corresponding display device(s) are identified or selected, the content or information currently being displayed at the display region(s) will be considered (or read). Subsequently, an arrangement or rearrangement process is performed to make space for the important message or other content or information of interest, within or along with the currently-displayed content or information, which is rearranged (e.g., with object displacements).

Also, to the extent that the currently-displayed content or information has a predominant color associated with it the important message or other content or information of interest being added for display will be shown in a new color that is different from that predominant color, such that the newly displayed information of interest will be highly visible to the vehicle operator (or other person or user) relative to the currently-displayed content or information (e.g., if the currently-displayed content or information shown on a display screen is predominantly red, then the newly displayed information of interest can be displayed in a markedly different color, such as green). Additionally, or instead, the newly displayed information can be displayed in a manner that takes in to account other factors such as lighting conditions (e.g., daytime or nighttime lighting conditions) experienced by the camera device. Thus, when an important message or other content or information of interest (e.g., an alarm or warning) occurs or is triggered that should be viewed by the vehicle operator, that information of interest is directed to the display region that is at or proximate to the location at which the vehicle operator is currently looking, and presented in a manner intended to highlight the information of interest for the vehicle operator and/or otherwise facilitate viewing of that information so that the vehicle operator is likely to view that information of interest.

Notwithstanding the modification of the displayed content or information to include the newly displayed information of interest, the system continues to monitor and determine the vehicle operator's line of sight (that is, the line of sight detection system will keep sending data). Consequently, if the vehicle operator over time changes his or her line of sight, the manner of displaying the newly displayed information of interest can also be modified over time to follow and accommodate the changing line of sight. Additionally, the system further is configured to detect if the vehicle operator has locked her or his sight on the important message or other content or information of interest (the newly displayed information of interest), where locking is determined to have occurred when the vehicle operator continues to look at the place where the newly displayed information of interest is being displayed for at least a predetermined amount of time (e.g., one second or more).

If the system determines that another predetermined amount of time has passed (typically more than one second, for example, ten seconds) and the vehicle operator has not yet locked his or her sight upon the information of interest, then the system causes one or more further easily-discernible signal(s) to be output, such as an audio signal and/or a steering rumbling/vibration signal, or possibly an additional highly-visible displayed signal. Any one or more (even all three) of these further easily-discernible signals) can continue to be provided until it is determined that the vehicle operator has locked his or her sight upon the information of interest. Also, in at least some embodiments, one or more buttons are made available in the vehicle, and the system concludes that the vehicle operator has viewed or otherwise adequately received the important message or other content or information of interest upon the vehicle operator pressing the appropriate button(s) as an acknowledgement that the vehicle operator has viewed or otherwise received that information of interest.

Figure 1:
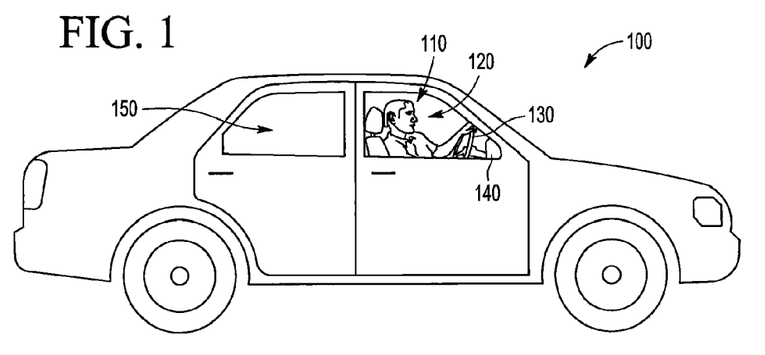
FIG. 1 is a schematic view of an example vehicle that, in accordance with an embodiment of the present disclosure, employs an improved system for facilitating the viewing of information in the vehicle.

Referring now to FIG. 1, a schematic side elevation view is provided of a vehicle 100 that in the present embodiment is an automobile. In accordance with the present disclosure, the vehicle 100 includes a region 110 within which is provided a system (see FIG. 2) for displaying information and facilitating the viewing of such displayed information by a vehicle operator (e.g., a driver of the vehicle) 120, who as shown can grasp a steering wheel 130 extending from a dashboard 140 of the vehicle. In the present example embodiment, each of the region 110, the system for displaying and facilitating the viewing of information (again see FIG. 2), the vehicle operator 120, the steering wheel 130, and the dashboard 140 all are generally situated within a cab 150 of the vehicle. Although the vehicle 100 of FIG. 1 is an automobile, it should be appreciated that the present disclosure also can encompass other vehicles including, for example, other motor vehicles such as trucks, motorcycles, off-road vehicles such as all-terrain vehicles, work vehicles such as agricultural vehicles or riding lawnmowers, as well as other types of vehicles such as boats, airplanes, helicopters, motorcycles, etc. Indeed, the present disclosure is also intended to encompass embodiments involving methods and systems for displaying and facilitating the viewing of information that are implemented in other circumstances and environments that do not involve vehicles including, for example, factories or installations in which information of interest relating to industrial control applications is being displayed to operators or other work personnel (e.g. in a control room of a factory or power facility such as a nuclear power plant).

Figure 2:
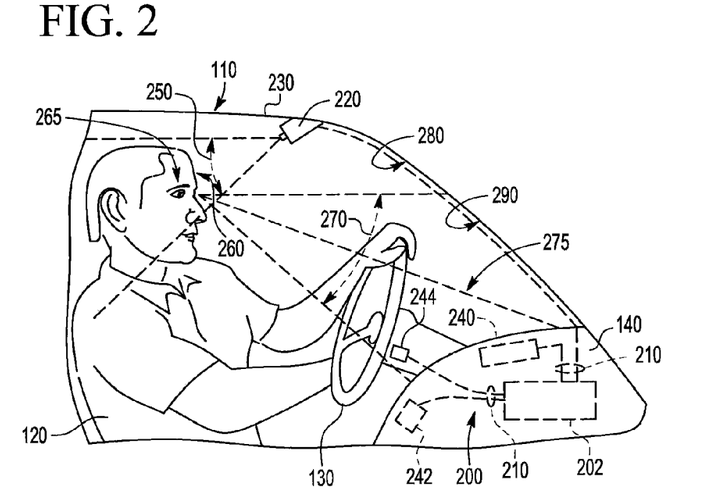
FIG. 2 is a schematic view of a portion of the vehicle of FIG. 1 that shows in more detail aspects of the system for facilitating the viewing of information in the vehicle.

Referring additionally to FIG. 2, a detail (partly cutaway) view is provided of the region 110 of FIG. 1 that shows with more particularity various components of the vehicle 100 that are situated within the vehicle cab 150 along with the vehicle operator 120. As already discussed, the vehicle 100 particularly includes the steering wheel 130 that extends from the dashboard 140 within the cab 150 of the vehicle, and FIG. 2 shows the vehicle operator 120 interacting with the steering wheel 130 extending from the dashboard 140.

Further, FIG. 2 also particularly includes components of the system for displaying and facilitating viewing of information, which are generally indicated by a reference numeral 200. More particularly in this regard, in accordance with the present embodiment, the system 200 includes a control device or processing unit 202 that is coupled at least indirectly by way of one or more communication links 210 to a camera device 220 that is mounted at or approximate to a ceiling region 230 of the cab 150 of the vehicle, and also is coupled at least indirectly by way of the one or more communication links 210 to one or more display devices 240. Additionally, the system 200 also includes one or more speakers 242 positioned on (or in) the dashboard 140 and a vibration device 244 affixed in relation to the steering wheel 130 (or at least the neck of the steering wheel by which the steering wheel is supported in relation to the dashboard 140), with each of the speakers and vibration device also being coupled at least indirectly by way of the one or more communication links 210 to the control device 202.

It should be appreciated that the one or more communication links 210 can be wired links or wireless communication links and can take any of a variety of physical paths depending upon the embodiment and thus the one or more communication links 210 are shown by way of dashed lines in FIG. 2. Also, as will be appreciated, the one or more display devices 240 can vary depending upon the embodiment in terms of the number, type, and positioning/arrangement of the display devices. Thus, although FIG. 2 shows the one or more display devices 240 by way of dashed lines showing a single box, this is intended to be representative of an embodiment, such as that discussed in further detail in FIG. 3, in which the one or more display devices 240 include multiple display devices that are arranged at numerous locations within the cab 150 and function in a variety of manners so as to result in the display of information for viewing by the vehicle operator 120 at numerous locations within the cab. Similarly, although FIG. 2 shows the one or more speakers 242 by way of dashed lines showing a single box, this is intended to be representative of a variety of different arrangements, including for example embodiments in which there are multiple speakers that are arranged at numerous locations along the dashboard 140 or elsewhere within the cab 150.

With respect to the control device 202, this also is intended to be representative of a variety of types of control devices depending upon the embodiment, as indicated by the dashed lines also used in FIG. 2 to show the control device (the dashed lines also indicate that the control device is positioned internally within the dashboard 140). In most embodiments including the present embodiment, the control device 202 includes both one or more processing devices and one or more memory devices. The processing devices can take a variety of forms such as, for example, one or more microprocessors and or graphic processing units, microcomputers, or application-specific integrated circuits. Although in some embodiments the control device 202 only includes a single processing device, in other embodiments multiple processing devices or distributed processors can be encompassed by the control device 202.

The memory devices can take any of a variety of forms (e.g., random access memory, read-only memory, dynamic random access memory, static random access memory, etc.), and can be used by the processing device(s) of the control device 202 for storing and retrieving data. In some embodiments, one or more of the processing devices can be integrated with one or more of the memory devices in a single device (e.g., a processor-in-memory (PIM)). Although shown to be positioned within the dashboard 140, in other embodiments the control device 202 (or one or more processing or memory devices thereof) can be positioned elsewhere within the vehicle 100. As will be appreciated, the one or more processing devices of the control device 202 is/are configured to perform operations in accordance with software programs or instructions, where the software programs or instructions can be stored on the one or more memory devices.

The camera device 220 also can take any of a variety of forms depending upon the embodiment. In some embodiments, the camera device 220 merely senses image data and communicates electronic signals indicative of such data to the control device 202, at which image processing or other processing can occur. In other embodiments, the camera device 220 can include one or more processing devices itself and/or can operate as a smart device capable of performing image processing or other processing itself. As illustrated, the camera device 220 has a range of view or field of view 250 and the camera device 220 is generally positioned so that the field of view 250 encompasses a face region 260 of the vehicle operator 120, and particularly includes eyes (one of which is shown) 265 of the vehicle operator.

Further as illustrated by FIG. 2, the vehicle operator 120 (or more particularly the vehicle operator's eyes 265) has an additional field of view 270 that encompasses a number of different regions along the dashboard 140 and above the dashboard along a windshield 280 of the vehicle. Additionally, the vehicle operator 120 can be said to have a line of sight 275 corresponding to a particular viewing angle within the field of view 270. It should be appreciated that the vehicle operator's field of view 270 can encompass, and the vehicle operator's line of sight 275 can be directed at (at least depending upon the position of the vehicle operator's face region 260 and eyes 265), various portions of the dashboard 140 that in the present embodiment encompass the one or more display devices 240, as well regions above the dashboard such as a region 290 along the windshield 280 along which displayed images can also be projected by way of the one or more of the display devices 240.

By virtue of eye tracking detection technology implemented in the camera device 220 and/or the control device 202 (e.g., similar or identical to eye tracking detection technology implemented in devices such as webcams), it is possible to obtain information/feedback as to the direction toward which the vehicle operator is looking. Such eye tracking detection technology can take a variety of forms depending upon the embodiment and should be understood to encompass a variety of technologies serving the same or substantially or largely similar purposes including, for example, gaze tracking technology or gaze direction (or gaze direction estimation) technology. Also, such eye tracking technology depending upon the embodiment can involve the implementation of one or more processes or subprocesses such as, further for example, facial detection, corner detection, eye detection, head posture analysis, pupil detection, edge detection, eye contour extraction, and/or other calibration, analysis, mathematical, or other types of processes or subprocesses, and further including among other things techniques and processes (and apparatuses and systems for performing such techniques and processes) as are described in any of the following, each of which is hereby incorporated by reference herein: "A Method of Gaze Direction Estimation Considering Head Posture" by Wan-zhi Zhang et al. (International Journal of Signal Processing, Image Processing and Pattern Recognition, Vol. 6, No. 2, April, 2013); "Gaze Tracking Using a Regular Web Camera" by David Jonathan Wild (Submission in partial fulfillment of the requirements of the degree of Bachelor of Science (Honours) of Rhodes University, Grahamstown, South Africa, November, 2012). Additionally, depending upon the embodiment, such eye tracking technology can also include one or more technologies such as OpenCV (Open Source Computer Vision Library) eye detection and tracking technology suitable for use with Android-based devices (where Android is made available by Google, Inc. of Mountain View, Calif.), as is discussed at http://romanhosek.cz/android-eye-detection-and-tracking-with-opencv/, and/or ITU Gaze Tracker technology developed at least in part by the IT University of Copenhagen (as is described at http://www.gazegroup.org/develop/).

Although the camera device 200 is shown to be a single camera device in the present embodiment, it should be appreciated that in other embodiments there can be employed more than a single camera device for monitoring the face region 260 and/or eyes 265 of a vehicle operator/driver or other person. The use of two camera devices allowing for stereo vision/monitoring can in some circumstances allow for calculation of a three dimensional position of the head of a vehicle operator (or other person), which can improve the accuracy with which the vehicle operator's line of sight is determined. Further, depending upon the embodiment, any of a variety of light sensing or monitoring technologies can be employed by any one or more camera devices that are employed, including for example technologies for sensing/monitoring visible light as well as technologies for sensing/monitoring infrared light/radiation. Also, in some embodiments in which multiple camera devices are employed, it is possible that a first camera device can utilize a first light sensing/monitoring technology and other camera device(s) can utilize one or more other light sensing/monitoring technology or technologies.

Figure 3:
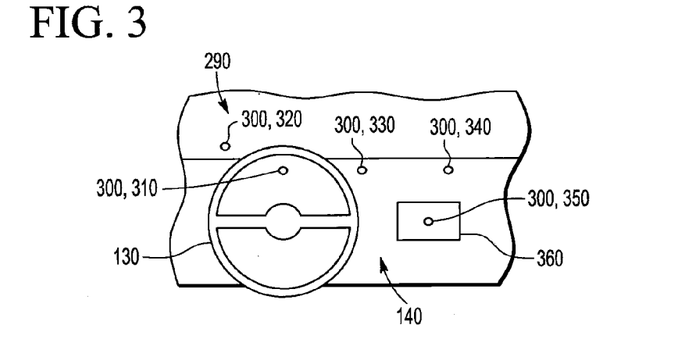
FIG. 3 is a further front elevation view of a further portion of the vehicle of FIGS. 1 and 2, particularly showing aspects of a dashboard, steering wheel, and windshield as viewed from within a cab of the vehicle.

FIG. 3 provides a further front elevation (partly cutaway) view of a portion of the dashboard 140 as well as the steering wheel 130 and the region 290 along the windshield region 280 to particularly illustrate display regions 300 that can be encompassed within the field of view 270 of the vehicle operator 120 (particularly as determined by the positioning of the vehicle operator's eyes 265). In the present example embodiment shown in FIG. 3, the display regions 300 include a first display region 310 forward of the steering wheel 130 that is visible through the steering wheel (by way of an orifice formed within the steering wheel), a second display region 320 that is located along the windshield 280 of the vehicle 100, third and fourth display regions 330 and 340, respectively, which are located at different positions along the dashboard 140 to the right of the steering wheel 130 proximate a top surface of the dashboard, and a fifth display region 350 located within a console region 360 on the dashboard 140.

The first, second, third, fourth, and fifth display regions 310, 320, 330, 340, and 350 encompassed by the display regions 300 are merely examples of possible display regions on the vehicle 100 and, depending upon the embodiment, one or more other display regions can be present and within a vehicle operator's field of view (such as the field of view 270) in addition to, or instead of, the display regions 310, 320, 330, 340, and 350. It should be appreciated that the physical locations of the display regions can, but need not always, coincide with the physical locations of the one or more display devices 240. For example, although the first, third, fourth, and fifth display regions 310, 330, 340, and 350 are along the dashboard and can be considered to correspond to (and be provided on) display screens of ones of the display devices 240 that are positioned at the locations of those regions, the second display region 320 along the region 290 along the windshield 280 can be considered to be merely a physical section of the windshield onto which light from one of the display devices (e.g., one of the display devices provided on the dashboard 140) is projected and off of which that light is reflected for viewing by the vehicle operator 120.

It should be noted, further in regard to the one or more display devices 240, that these display devices can take any of a variety of one or more different forms depending upon the embodiment or implementation. For example, any of the one or more display devices 240 can be a light emitting diode (LED) display, a liquid-crystal display (LCD), a thin-film-transistor (TFT) display (or a thin-film-transistor liquid-crystal display or TFT LCD), a Cathode ray tube (CRT) display, or a television, and such one or more display devices can be positioned on the dashboard 140, on a console, on the steering wheel, or on or at any of variety of other structures or regions/portions of the vehicle, for example, structures or regions/portions that are operator-accessible or can be within a field of view of (or can be viewed by) an operator or other person within or associated with the vehicle. Also for example, any of the one or more display devices 240 can be a projector or other display device that projects images at locations apart from the location of the projector/other display device itself, e.g., projects images at locations that are within a field of view of (or can be viewed by) an operator or other person within or associated with the vehicle.

Thus, depending upon the embodiment, each of the one or more display devices 240 can operate to display images at a respective display region (or potentially multiple respective display regions) such as any of the display regions 310, 320, 330, 340, and 350 that is (or are) existing on surface(s) of or within the respective display device itself or at a location (or multiple locations) apart from the location of the display device itself, such as upon the windshield or upon an interior wall or surface (e.g., of the dashboard or elsewhere) upon which image(s) can be effectively displayed. The display devices 240 can be, for example, display devices that normally or sometimes operate to display any of a variety of types of information including, for example, radio station information, temperature, direction, time (clock), or map information, or any of a variety of types of operational status information including, for example, vehicle operational status information such as odometer information, speedometer or engine rotations per minute information, engine temperature or pressure readings information, etc.

Figure 4:
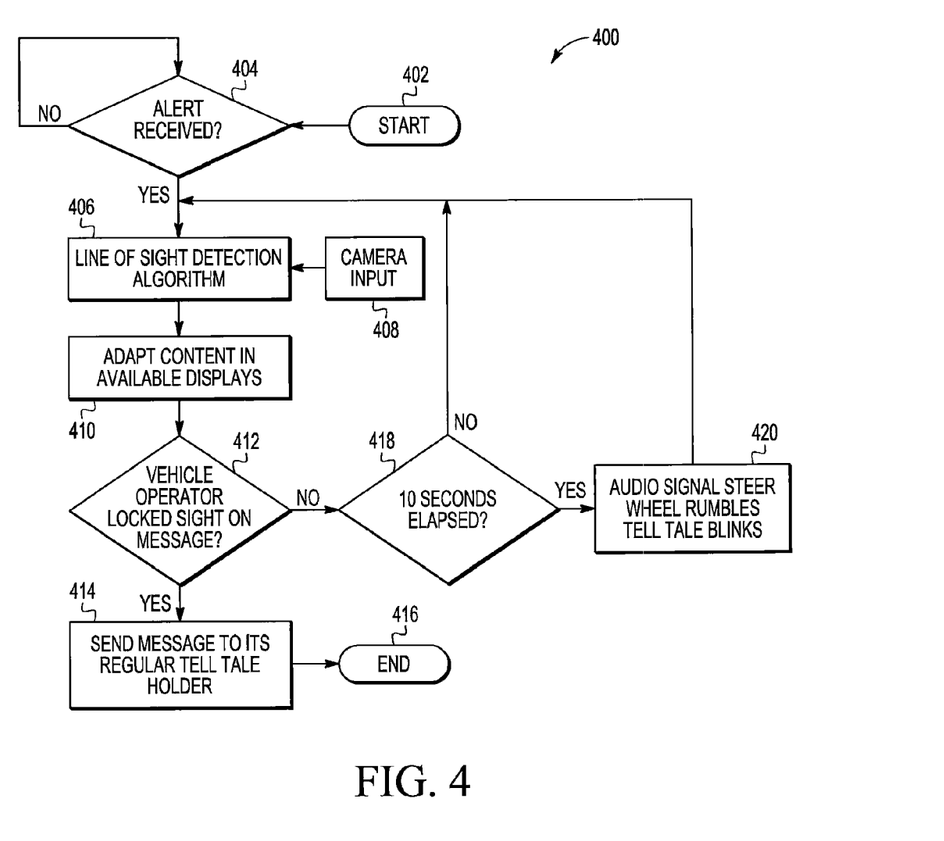
FIG. 4 is a flow chart illustrating example steps of an improved method for facilitating the viewing of information in the vehicle of FIGS. 1-3.

As mentioned above, the present disclosure envisions that a system such as the system 200 operates to display information and facilitate the viewing of information by a person or user such as the vehicle operator 120 within or associated with a vehicle such as the vehicle 100. Turning to FIG. 4, a flow chart 400 is provided showing example steps of a method or process of operation of the system 200 of FIGS. 1-3 in this regard. More particularly as shown, upon the flow chart 400 beginning at a start step for 402, it is first determined at a step 404 whether an alert has been received at the control device 202 indicating that a message or other information should be communicated to the vehicle operator 120. Until an alert has been received, the process remains at the step 404. However, upon an alert being received, the process advances to a step 406. It should be noted that, although the step 404 concerns receipt of an alert by the control device 202 from some other circuit, component, device (e.g., sensor), or entity (e.g., another control or processing device), in other circumstances or embodiments alerts can be determined by the control device 202 itself based upon its own processing or interpretation of received information. Also, in some other embodiments, no alert need be received but rather the step 404 can be skipped.

Upon the process reaching the step 406, the control device 202 then receives input information from the camera device 220 (e.g., via the one or more communication links 210) as represented by a step 408 and processes that information in accordance with a line of sight detection algorithm so as to determine the vehicle operator's line of sight 275. Alternatively, a field of view detection algorithm is employed instead of, or in addition to, the line of sight detection algorithm so that the vehicle operator's field of view 270 is determined instead or in addition to the vehicle operator's line of sight 275. The information provided by the camera device 220 as represented by the step 408 is particularly information relating to the positions or orientations of the vehicle operator's eyes 265, which as discussed with reference to FIG. 2 are within the field of view 250 of the camera device.

Although in the present embodiment it is envisioned that the control device 202 performs the line of sight processing, in other embodiments the line of sight processing can be performed by the camera device 220 and the control device 202 merely utilizes line of sight information provided by the camera device to generate control signals for the display devices (or to take other actions). Indeed, depending upon the embodiment, various types of image processing and/or other processing can be performed by the control device 202, the camera device 220, and/or possibly by way of other devices (e.g., other processing devices), in a variety of different manners. Correspondingly, the information communicated between the camera device 220 and the control device 202 can vary depending upon the embodiment. In some embodiments, the information that is communicated therebetween can be raw image data (e.g. indicative of eye position) that is then processed by the control device to determine a line of sight. In other embodiments, the information that is communicated can be visual image information that has already been processed, or line of sight information (e.g., if the processing involving the line of sight algorithm is performed by the camera device 220 itself).

Once the vehicle operator's line of sight 275 (and/or field of view 270) has been determined by way of processing performed in accordance with the line of sight detection algorithm (and/or field of view detection algorithm) at the step 406, then the process further advances to a step 410. At the step 410, the control device 202 causes the displaying of the message or other content or information of interest within the one or more display regions 300 by way of (directly or indirectly, e.g., by way of projection) the one or more of the display devices 240 to be modified to suit the vehicle operator's line of sight 275 (and/or field of view 270). Such modification of the manner of display increases the likelihood that the content or information being displayed will be viewed by the vehicle operator 120. For example, with reference to FIGS. 2 and 3, in one operational circumstance it can be the case that initially information is displayed at the second display region 320 along the region 290 of the windshield 280 but at the step 406 it is determined that the vehicle operator's line of sight 275 (at least temporarily) is directed at a location proximate the top of the dashboard 140. In such case, the control device 202 can cause the one or more display devices 240 to shift in operation so that, rather than the information being displayed at the second display region 320, the information instead is displayed at one or both of the third and fourth display regions 330 and 340 that are proximate the top of the dashboard.

Next, at a step 412, the control device 202 determines whether the vehicle operator 120 (or other person or user) has locked his or her sight onto the message or other content or information of interest, that is, locked his or her sight onto that one (or possibly more than one) of the display regions 300 associated with the one or more display devices 240 at which, in accordance with the step 410, that content or information of interest is being displayed. The vehicle operator 120 particularly is determined to have locked his or her sight onto the message or other content or information of interest if it is determined, based upon the signals received by the control device 202 from the camera device 220, that the vehicle operator's line of sight 275 has been continuously or substantially continuously directed toward that content or information of interest (that is, directed toward the display region at which that content or information is being displayed) for a predetermined amount of time.

If at the step 412 it is determined the vehicle operator 120 (or other person or user) has locked his or her sight onto the displayed message or other content or information of interest, then the process advances to a step 414, at which the message or other content or information of interest is sent to its regular telltale holder, and then the process ends a step 416. Alternatively, if at the step 412 it is determined that the vehicle operator 120 has not locked his or her sight on the message or other content or information of interest, then the process advances to a step 418. At the step 418, it is determined whether a predetermined amount of time has yet elapsed since the alert was determined to have been received at the step 412. The predetermined amount of time can vary depending upon the circumstance or embodiment and, in the present example embodiment, is ten seconds. Also, although in the present embodiment the elapsing of the predetermined amount of time is measured with respect to the time at which the alert was determined to have been received, in other embodiments the elapsing of the predetermined amount of time can be measured with respect to some other event or base time such as, for example, the time at which the manner of display of the content or information of interest was modified at the step 410.

As further shown in FIG. 4, if it is determined at the step 418 that the predetermined amount of time (again, in this example, ten seconds) has not yet elapsed, then the process returns from the step 418 back to the step 406. Thus, the line of sight of the vehicle operator 120 is again determined and, if the line of sight has changed since the previous time at which it was determined, then at the step 410 the manner of display of the message or other content or other information of interest is again adapted to conform to the new line of sight. And, again, at the step 412 it is determined again whether the vehicle operator 120 has locked his or her sight onto the message or other content or information of interest and, if not, the process returns to the step 418. Thus, until the predetermined amount of time has elapsed as determined at the step 418, the steps 406, 408, 410, 412, and 418 can be repeated multiple times unless it is determined, at the step 412, that the vehicle operator 120 has locked his or sight onto the message or other content or information of interest (in which case the process advances to the steps 414 and 416 as discussed above).

However, if at the step 418 it is determined that the predetermined amount of time has elapsed (in this example, that more than ten seconds has elapsed) since the time of the alert being received at the step 404, then the process advances to a step 420, at which one or more actions are taken under the control of the control device 202 that are intended to cause the vehicle operator 120 to take note of, and ultimately view, the message or other content or information of interest. As indicated at the step 420 of FIG. 4, in the present example embodiment, such actions can include, for example, one or more of actuating the vibration device 244 to cause the steering wheel 130 to rumble, actuating the one or more speakers 242 to output a loud noise that is discernible by the vehicle operator 120, and/or actuating the one or more display devices 240 so as to provide a highly visible signal such as a telltale blinking signal.

Upon completion of the step 420, the control device 202 of the system 200 again attempts to determine whether the vehicle operator 120 has viewed the message or other content of interest by way of reperforming the steps 406, 410, and 412. Again, if at the step 412 it is still determined that the vehicle operator 120 has not yet locked his or her sight upon the message or other content or information of interest, the process again advances to the step 418. Thus, in the present embodiment, the steps 406, 410, 412, 418, and 420 are repeated indefinitely until it has been determined that the vehicle operator 120 has locked his or her sight upon the message or other content or information of interest, and the message or other content or information of interest continues to be displayed until such a determination is made, with the determination serving as an indication that the vehicle operator 120 has in fact viewed the information of interest or at least an indication that the vehicle operator has probably or likely viewed the information of interest. Notwithstanding this manner of operation, in alternate embodiments a modified version of the process of FIG. 4 can be performed in which, upon performing of the step 420, the control device 202 presumes that the output provided at the step 420 has been sufficient to cause the vehicle operator 120 to view the information of interest, and consequently the process ends at the end step 416 immediately after the performing of the step 420.

Also, in some alternate embodiments the system can cease displaying information of interest, even though it has not been determined yet that the message or other content or information of interest has been viewed, because some other condition has been met or some other determination has been made. For example, in some embodiments or circumstances, the message or other content or information of interest can include one or more warning messages (e.g., an engine overheating warning or temperature around freeze level warning), and yet such warning messages can at some point become obsolete regardless of whether a vehicle operator has viewed those messages. If the reason(s) for the warning messages are no longer applicable (e.g., because the engine is no longer overheating or the temperature is no longer around a freezing level), then the system can cease to display those warning messages even though the messages have not yet been viewed by the vehicle operator. Additionally, in some further alternate embodiments, even though the system has not yet determined that a given message or other content or information of interest being displayed has been viewed, and even though the reason(s) for displaying that content or information of interest continue to exist, there can arise circumstances in which the displaying of that information should be at least temporarily stopped (e.g., where that information disappears from view). For example, in some such embodiments, the displaying of such content or information could be temporarily ended because other information of greater interest or importance (e.g., a more urgent warning message) has arisen and should be displayed first.

Figure 5:
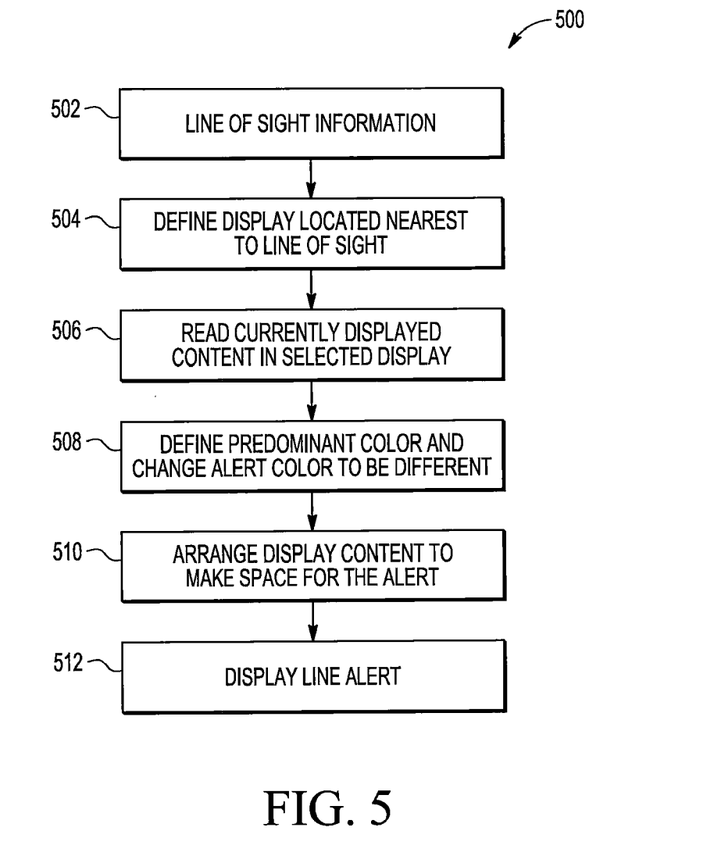
FIGS. 5 and 6 are additional flow charts illustrating various substeps of some of the steps of the flow chart of FIG. 4.

Turning to FIG. 5, a further flow chart 500 is provided that shows example substeps of a subprocess corresponding particularly to the step 410 of the flow chart 400 of FIG. 4, with the subprocess concerning adaptation of the manner of display of the content or information of interest at the one or more display regions 300 by way of the one or more display devices 240. As shown, the flow chart 500 begins at a substep 502 in which the line of sight (and/or field of view) information determined at the step 406 is received (or otherwise obtained) at the control device 202. It should be appreciated that the line of sight (and/or field of view) information pertaining to the vehicle operator 120 is useful in determining which of the display regions 300 the vehicle operator is, or probably or likely is, looking at. Therefore, subsequent to the substep 502, at a substep 504 the control device 202 determines or defines that one or more of the display regions 300 that is or are located closest to the line of sight of the vehicle operator. Correspondingly, the control device 202 determined defines that one or more of the display devices 240 that corresponds to those one or more display regions 300, either because the display regions directly correspond to the location of the display devices or because the display devices govern the displaying that occurs at those display regions (again, for example, because the display device projects light toward the display region).

Next, at a substep 506, the control device 202 analyzes the content or information that is currently being displayed at the display region(s) 300 by the display device(s) 240 determined (or defined) at the step 504. Further, at a substep 508, the control device 202 particularly determines or defines a predominant color associated with that content or information that is currently being displayed at the display region(s) 300 by the display device(s) and, upon making that determination, the control device 202 changes an alert color to be different than (and contrasting with respect to) the predominant color. Then additionally, at a substep 510, the control device 202 causes the content or information that is currently being displayed at the display region(s) 300 by the display device(s) 240 determined at the step 504 to be rearranged so as to make a space (or spaces) for the message or other content or information of interest that is the subject of the alert received at the step 404. Finally, at a substep 512 of the flow chart 500, the message or other content or information that is the subject of the alert is displayed at the display region(s) 300 by the display device(s) 240. The display of this message or other content or information is in accordance with the alert color determined at the substep 508 and occurs within the space(s) determined at the substep 510.

Figure 6:
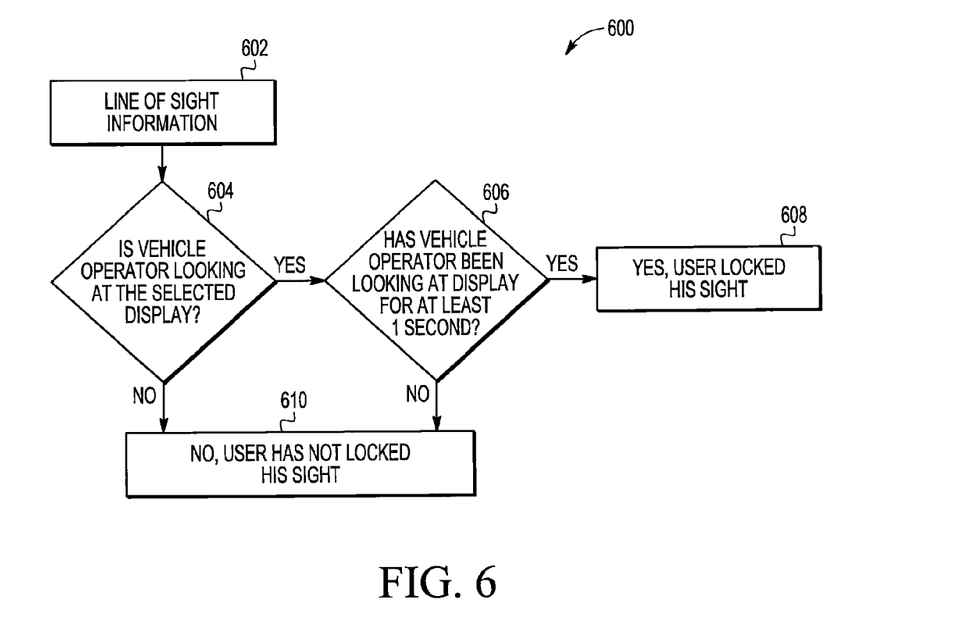

Turning to FIG. 6, an additional flow chart 600 shows additional substeps of the flow chart 400, particularly corresponding to the step 412, at which the control device 202 determines whether the vehicle operator 120 has locked his or her sight on the message or other content or information of interest. The subprocess represented by the flow chart 600 begins at a substep 602 in which the information concerning the line of sight of the vehicle operator 120 (e.g., the line of sight 275) sensed by way of the camera device 220 is obtained by the control device 202 by way of signal(s) provided from the camera device via the one or more communication links 210. Then, at a substep 604, the control device 202 determines, based upon the line of sight information, whether the vehicle operator 120 is looking at the display region(s) 300 that are displaying the message or other content or information of interest. As already noted, the displaying of the message or other content or information of interest at a selected one or more of the display region(s) 300 is performed by the display device(s) 240 that govern the displaying of information at those display region(s), in accordance with the step 410 and, in at least some embodiments, in accordance with the substeps of the flow chart 500 of FIG. 5 as discussed above.

It should be noted that the determination, by the control device 202 at the substep 604, can be performed in any of a variety of manners depending upon the embodiment. For example, in at least some embodiments, the control device 202 can determine whether the line of sight of the vehicle operator 120 is directed toward, or at least within a predetermined angular variation (e.g., within plus or minus 10 degrees) of being directed toward, a particular one of the display regions 300 at which the information of interest is being displayed. Also, in other alternate embodiments in which it is the vehicle operator's field of view (such as the field of view 270) that is determined at the substep 602, the control device 202 at the substep 604 can determine whether the location of the display region 300 at which the information of interest is being displayed is within the angular range of that field of view.

If it is determined at the substep 604 that the vehicle operator is looking at the display region(s) 300 at which the information of interest is being displayed, then the subprocess advances to a substep 606 at which the control device 202 further determines whether the vehicle operator has been looking at the display region(s) for at least a predetermined amount of time, for example, one second. If this is in fact the case, then the process advances to a substep 608, at which the control device 202 determines that, indeed, the vehicle operator has locked his or her sight onto the display region(s) and thus locked his or her sight onto the message or other content or information of interest. If this is the result, then as indicated by FIG. 4 the process of the flow chart 400 proceeds from the step 412 to the step 414 as already discussed above. Alternatively, if it is determined either at the substep 604 that the vehicle operator is not looking at the display region(s) 300 at which the information of interest is being displayed, or at the substep 606 that the vehicle operator has not been looking at the display region(s) for at least the predetermined amount of time considered at that substep (again, in this example, one second), then the subprocess advances from the step 604 or the step 606 to a step 610 at which it is concluded that the vehicle operator has not locked his or her sight on the information of interest. If this is the result, then as indicated by FIG. 4, the process of the flow chart 400 proceeds from the step 412 to the step 418 as already discussed above.

It should be appreciated that the above-described embodiments and other embodiments encompassed herein are advantageous in numerous respects. Among other things, such embodiments facilitate the viewing of information of interest by vehicle operators (or other persons or users within or associated with a vehicle) by adjusting the displaying of such information of interest based upon the sensed viewing behavior of the vehicle operators. Also, such embodiments facilitate the viewing of such information of interest by taking extra steps to monitor whether the vehicle operators' behavior suggests that the information has been viewed and received by the vehicle operators, to adjust the displaying of the information when then the vehicle operators' viewing behavior changes, and/or to provide additional special sound, tactile/vibrational, and/or visual notifications or alerts when the vehicle operators' viewing behavior appears not to be indicating that the vehicle operators have actually viewed or received in the information of interest. In at least some embodiments, the system only presumes that the vehicle operators have actually viewed or otherwise received the information of interest when it is determined that the vehicle operators' viewing behavior is consistent with the vehicle operators' focusing, their attention upon the information of interest for a sufficiently-long time that it is probable or likely that the vehicle operators have in fact viewed or otherwise received the information or, alternatively, only if either such a determination has been made or another signal has been received (e.g., a signal from a button pressed by the vehicle operator confirming the vehicle operator's receipt of the information of interest).

It should be appreciated that at least some embodiments disclosed herein can facilitate the likelihood that vehicle operators (or other persons associated with vehicles) will receive or appreciate the significance of important (or even critical) messages or other information of interest, and/or reduce the likelihood that vehicle operators (or other persons associated with vehicles) will miss or fail to appreciate the significance of important (or even critical) messages or other information of interest. By virtue of such operation, such embodiments can directly or indirectly result in a number of positive benefits including, for example, enhancements in vehicle operation or performance, enhancements in the driving experiences of vehicle operators (or other persons associated with vehicles), enhancements in vehicular safety, and otherwise. That said, although it is envisioned that various embodiments encompassed herein can have any of a variety of beneficial effects, nothing discussed or disclosed herein should be viewed as constituting or providing any guarantee that any particular beneficial effect(s) will be realized or achieved by any particular embodiments encompassed herein, or that any particular embodiment encompassed herein will result in safe operation of a vehicle or other system or that other vehicles or systems will produce unsafe operation. Safety and safe operation in particular depend upon a wide variety of factors outside of the scope of the present disclosure including, for example, numerous other features of vehicular or other systems as well as the manner in which vehicles or other systems are operated or maintained. Further, it should again be understood that the present disclosure pertains not only to embodiments involving vehicles but also to embodiments or implementations involving machines other than vehicles, e.g., machines in other environments or contexts in which there is displaying of information to be viewed by machine operator(s) or other persons associated with the machines.

It should be appreciated that the present disclosure is intended to encompass numerous embodiments. For example, in one embodiment, the present disclosure relates to a method of facilitating viewing of first information by a machine user. The method includes (a) determining second information concerning a viewing direction of the machine user, and (b) adapting at least one operation of at least one display device so as to display the first information, based at least in part upon the determined second information. Also, in an additional embodiment, the method includes (c) additionally determining whether a first condition has been met, where the first condition is indicative of whether the machine user has failed to view in a sufficient manner the first information for or during a first predetermined amount of time, and (d) upon the first condition being additionally determined to have been met, one or both of (i) repeating (a), (b), and (c), and (ii) outputting a signal configured to be sensed by the machine user to increase a likelihood that the machine user will view in the sufficient manner the first information.

Additionally, in a further example embodiment, the method is performed within a vehicle and the machine user is a vehicle user, and the method further comprises obtaining position information of an eye of the vehicle user by way of a camera device, where the second information is determined at least in part based upon the obtained position information. Also, in an additional embodiment, the second information is determined based in part upon a line of sight detection algorithm utilized by a processing device at least indirectly associated with the camera device. Further, in an additional embodiment, the method further comprises receiving the first information at a first time, and wherein the first condition is determined to have been met when the first predetermined amount of time is determined to have elapsed since the first time without it being otherwise determined that the vehicle user has viewed the first information for a second predetermined amount of time during the first predetermined amount of time.

Also, in a further embodiment of the above-discussed method, the outputting of the at least one signal includes either causing a sound to be output by a speaker or a vibrational output to be provided by a vibrational device. In another embodiment, the first condition is determined to have been met when it is determined based upon the second information that the machine user has not viewed the first information continuously or substantially continuously for the first predetermined amount of time. In a further embodiment, the second information concerning the viewing direction is indicative of either a line of sight of at least one eye of the machine user, or a field of view of the machine user.

In an additional embodiment, the method discussed above is performed within a vehicle and the machine user is a vehicle user, and the method further comprises actuating the at least one display device to either display on the at least one display device, or to project onto a windshield or other surface of the vehicle, first image portions prior to (b) (of the method as discussed above), and wherein the vehicle user is either a driver or a passenger. In a further embodiment, (b) (of the method as discussed above) includes one or both of: (1) determining a predominant color associated with first image portions displayed by the at least one display device, determining an additional color differing from the predominant color, and causing the at least one display device to display the first information in the additional color; and (2) causing the at least one display device to modify a manner of displaying the first image portions so that one or more regions are formed in relation to the first image portions and so that the first information is displayed within the one or more regions.

In a further example embodiment, the present disclosure relates to a system for facilitating viewing of first information by a machine user who is present proximate to or within a machine. The system comprising includes a camera device configured for being supported in relation to the machine, the camera device further being configured to obtain position information that is at least indirectly representative of a position of at least one portion of a body of the machine user. The system also includes one or more display devices configured to cause displaying of one or more image portions at one or more display regions positioned on or along a region of the machine which can be within a field of view of the machine user. The system further includes at least one processing device coupled at least indirectly to each of the camera device and the one or more display devices, the at least one processing device configured to receive further information provided from the camera device that is at least partly based upon the position information and configured to generate one or more control signals to be provided to the one or more display devices to cause the one or more display devices to modify the displaying of the one or more image portions so that the modified one or more image portions show the first information arranged in a manner that is suited to facilitate viewing of the first information by the machine user based upon the further information provided from the camera device.

In an additional embodiment, the system is such that the at least one processing device is configured to determine whether, based upon the at least one signal, the position of the at least one portion of the body of the vehicle user is indicative of the vehicle user having viewed the first information. Further, in another embodiment, the system further comprises at least one output device coupled at least indirectly to the at least one processing device, wherein the at least one output device includes one or more of a speaker and a vibration output device. Also, in another embodiment of the above-discussed system, the at least one processing device is additionally configured to repeatedly determine over a first time period whether, based upon the at least one signal, the position of the at least one portion of the body of the vehicle user is indicative of the vehicle user having viewed the first information, and the at least one processing device is further configured to send at least one output signal to the at least one output device causing actuation of the at least one output device if the first time period expires but the at least one processing device has not yet determined that the position of the at least one portion of the body of the vehicle operator is indicative of the vehicle user having viewed the first information.

Further, in another embodiment of the above-discussed system, either the camera device or the at least one processing device is configured to determine a line of sight of the vehicle user based upon the position information, based at least in part upon a line of sight detection algorithm, and the vehicle user is a vehicle operator and the portion of the body is at least one eye of the vehicle operator. Also, in another embodiment, the one or more control signals are configured to cause the one or more display devices to modify the displaying of the one or more image portions so that either (a) the first information as displayed in the modified one or more image portions has substantially a different color than a predominant color associated with remaining portions of the modified one or more image portions, or (b) the one or more image portions are modified so as to include one or more regions within which the first information is displayed, the one or more regions not being present within the one or more image portions prior to the one or more image portions being modified. Additionally, the present disclosure also encompasses an automobile comprising the above-discussed system, where the vehicle is the automobile, and where the camera device is supported within a cab of the vehicle and oriented so that a field of view of the camera device encompasses the portion of the body of the vehicle user.

Further, in at least one additional embodiment, the present disclosure relates to a method of facilitating viewing of first information by a machine user associated with a machine. The method includes: (a) displaying second information by way of at least one display device associated with the machine; (b) receiving the first information; (c) determining third information concerning a viewing direction of the machine user; (d) adapting at least one operation of the at least one display device so as to display the first information, based at least indirectly upon the determined third information; and (e) additionally determining by way of a first processing device whether the machine user has viewed continuously or substantially continuously the first information for a first predetermined amount of time.

In an additional embodiment, the above-described method further comprises (t) if it is determined at (e) that the machine user has not viewed continuously or substantially continuously the first information for the first predetermined amount of time, then repeating (c), (d), and (e). Further, in another embodiment, the adapting of (d) (of the above-discussed method) includes modifying the displaying of the second information so that at least one space is included among portions of the displayed second information within which can be displayed the first information, such that the first information is displayed in addition to some or all of the second information, and the method further comprises at least one of (1) outputting an audio sound, (2) providing a vibrational output, and (3) providing an additional displayed image portion if it is further determined that a second predetermined amount of time has passed since (b).

While the principles of the invention have been described above in connection with specific apparatus, it is to be clearly understood that this description is made only by way of example and not as a limitation on the scope of the invention. It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A method of facilitating viewing of first information by a machine user, the method comprising:
   a) determining second information concerning a viewing direction of the machine user;
   b) adapting at least one operation of at least one display device so as to display the first information, based at least in part upon the determined second information; and
   c) additionally determining whether a first condition has been met, wherein the first condition is indicative of whether the machine user has failed to view in a sufficient manner the first information for or during a first predetermined amount of time.

2. The method of claim 1, further comprising:
   d) upon the first condition being additionally determined to have been met, one or both of:
      i) repeating (a), (b), and (c), and
      ii) outputting a signal configured to be sensed by the machine user to increase a likelihood that the machine user will view in the sufficient manner the first information.

3. The method of claim 2, wherein the method is performed within a vehicle and the machine user is a vehicle user, and further comprising:
   obtaining position information of an eye of the vehicle user by way of a camera device, wherein the second information is determined at least in part based upon the obtained position information.

4. The method of claim 3, wherein the second information is determined based in part upon a line of sight detection algorithm utilized by a processing device at least indirectly associated with the camera device.

5. The method of claim 2, further comprising:
   receiving the first information at a first time, and
   wherein the first condition is determined to have been met when the first predetermined amount of time is determined to have elapsed since the first time without it being otherwise determined that the vehicle user has viewed the first information for a second predetermined amount of time during the first predetermined amount of time.

6. The method of claim 5, wherein the outputting the signal includes either causing a sound to be output by a speaker or a vibrational output to be provided by a vibrational device.

7. The method of claim 2, wherein the first condition is determined to have been met when it is determined based upon the second information that the machine user has not viewed the first information continuously or substantially continuously for the first predetermined amount of time.

8. The method of claim 1, wherein the second information concerning the viewing direction is indicative of either a line of sight of at least one eye of the machine user, or a field of view of the machine user.

9. The method of claim 1, wherein the method is performed within a vehicle and the machine user is a vehicle user, and further comprising
   actuating the at least one display device to either display on the at least one display device, or to project onto a windshield or other surface of the vehicle, first image portions prior to (b), and wherein the vehicle user is either a driver or a passenger.

10. The method of claim 1, wherein (b) includes one or both of:
    1) determining a predominant color associated with first image portions displayed by the at least one display device, determining an additional color differing from the predominant color, and causing the at least one display device to display the first information in the additional color; and
    2) causing the at least one display device to modify a manner of displaying the first image portions so that one or more regions are formed in relation to the first image portions and so that the first information is displayed within the one or more regions.

11. A system for facilitating viewing of first information by a machine user who is present proximate to or within a machine, the system comprising:
    a camera device configured for being supported in relation to the machine, the camera device further being configured to obtain position information that is at least indirectly representative of a position of at least one portion of a body of the machine user;
    one or more display devices configured to cause displaying of one or more image portions at one or more display regions positioned on or along a region of the machine which can be within a field of view of the machine user; and
    at least one processing device coupled at least indirectly to each of the camera device and the one or more display devices, the at least one processing device configured to receive further information provided from the camera device that is at least partly based upon the position information and configured to generate one or more control signals to be provided to the one or more display devices to cause the one or more display devices to modify the displaying of the one or more image portions so that the modified one or more image portions show the first information arranged in a manner that is suited to facilitate viewing of the first information by the machine user based upon the further information provided from the camera device, wherein the at least one processing device is additionally configured to repeatedly determine over a first time period whether, based upon the one or more control signals, the position of the at least one portion of the body of the machine user is indicative of the machine user having viewed the first information.

12. The system of claim 11, wherein the at least one processing device is configured to determine whether, based upon the one or more control signals, the position of the at least one portion of the body of the machine user is indicative of the machine user having viewed the first information.

13. The system of claim 12, further comprising at least one output device coupled at least indirectly to the at least one processing device, wherein the at least one output device includes one or more of a speaker and a vibration output device.

14. The system of claim 13,
    wherein the at least one processing device is further configured to send at least one output signal to the at least one output device causing actuation of the at least one output device if the first time period expires but the at least one processing device has not yet determined that the position of the at least one portion of the body of the machine user is indicative of the machine user having viewed the first information.

15. The system of claim 11, wherein either the camera device or the at least one processing device is configured to determine a line of sight of the machine user based upon the position information, based at least in part upon a line of sight detection algorithm, wherein the machine user is a vehicle operator and the portion of the body is at least one eye of the vehicle operator.

16. The system of claim 11, wherein the one or more control signals are configured to cause the one or more display devices to modify the displaying of the one or more image portions so that either (a) the first information as displayed in the modified one or more image portions has substantially a different color than a predominant color associated with remaining portions of the modified one or more image portions, or (b) the one or more image portions are modified so as to include one or more regions within which the first information is displayed, the one or more regions not being present within the one or more image portions prior to the one or more image portions being modified.

17. An automobile comprising the system of claim 11, wherein the machine is the automobile, wherein the machine user is a vehicle user, and wherein the camera device is supported within a cab of the vehicle and oriented so that a field of view of the camera device encompasses the portion of the body of the vehicle user.

18. A method of facilitating viewing of first information by a machine user associated with a machine, the method comprising:
   a) displaying second information by way of at least one display device associated with the machine;
   b) receiving the first information;
   c) determining third information concerning a viewing direction of the machine user;
   d) adapting at least one operation of the at least one display device so as to display the first information, based at least indirectly upon the determined third information; and
   e) additionally determining by way of a first processing device whether the machine user has viewed continuously or substantially continuously the first information for a first predetermined amount of time.

19. The method of claim 18, further comprising:
   f) if it is determined at (e) that the machine user has not viewed continuously or substantially continuously the first information for the first predetermined amount of time, then repeating (c), (d), and (e).

20. The method of claim 19, wherein the adapting of (d) includes modifying the displaying of the second information so that at least one space is included among portions of the displayed second information within which can be displayed the first information, such that the first information is displayed in addition to some or all of the second information, and wherein the method further comprises at least one of (1) outputting an audio sound, (2) providing a vibrational output, and (3) providing an additional displayed image portion if it is further determined that a second predetermined amount of time has passed since (b).

* * * * *